United States Patent
Lupia et al.

(10) Patent No.: US 9,358,195 B2
(45) Date of Patent: *Jun. 7, 2016

(54) STABILIZED BODY CARE PRODUCTS, HOUSEHOLD PRODUCTS, TEXTILES AND FABRICS

(75) Inventors: Joseph Anthony Lupia, Reinach (CH); Joseph Suhadolnik, Yorktown Heights, NY (US)

(73) Assignee: BASF SE, Ludwigshafen (DE)

( * ) Notice: Subject to any disclaimer, the term of this patent is extended or adjusted under 35 U.S.C. 154(b) by 2435 days.

This patent is subject to a terminal disclaimer.

(21) Appl. No.: 10/512,528

(22) PCT Filed: Apr. 24, 2003

(86) PCT No.: PCT/EP03/04262
§ 371 (c)(1),
(2), (4) Date: Oct. 21, 2004

(87) PCT Pub. No.: WO03/103622
PCT Pub. Date: Dec. 18, 2003

(65) Prior Publication Data
US 2005/0220727 A1    Oct. 6, 2005

Related U.S. Application Data

(60) Provisional application No. 60/377,381, filed on May 2, 2002.

(51) Int. Cl.
| | |
|---|---|
| *A61K 9/00* | (2006.01) |
| *A61K 8/41* | (2006.01) |
| *A61K 8/49* | (2006.01) |
| *A61Q 5/00* | (2006.01) |
| *A61Q 5/02* | (2006.01) |
| *A61Q 5/06* | (2006.01) |
| *A61Q 19/00* | (2006.01) |

(52) U.S. Cl.
CPC . *A61K 8/41* (2013.01); *A61K 8/416* (2013.01); *A61K 8/4926* (2013.01); *A61Q 5/008* (2013.01); *A61Q 5/02* (2013.01); *A61Q 5/06* (2013.01); *A61Q 19/00* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 4,786,431 A | 11/1988 | Broze et al. | 510/304 |
| 6,187,387 B1 | 2/2001 | Bolle et al. | |
| 6,254,724 B1 * | 7/2001 | Seltzer et al. | 162/70 |
| 6,500,303 B1 | 12/2002 | Seltzer et al. | |
| 2004/0013619 A1 * | 1/2004 | Reinehr et al. | 424/59 |

FOREIGN PATENT DOCUMENTS

| | | | |
|---|---|---|---|
| EP | 0157738 | | 10/1985 |
| EP | 0309401 | | 3/1989 |
| FR | 2579615 | | 10/1986 |
| GB | WO 0107550 | * | 2/2001 |
| WO | 96/15110 | | 5/1996 |
| WO | 9905108 | | 2/1999 |
| WO | 01/07550 | | 2/2001 |
| WO | 01/85857 | | 11/2001 |

* cited by examiner

*Primary Examiner* — Snigdha Maewall
(74) *Attorney, Agent, or Firm* — Howard & Howard Attorneys PLLC

(57) ABSTRACT

Disclosed are stabilized body care products, household products, textiles and fabrics which comprise certain hindered nitroxyl, hydroxylamine and hydroxylamine salt compounds. Dyed products and articles are effectively stabilized against color degradation. The products are for example skin-care products, hair-care products, dentifrices, cosmetics, laundry detergents and fabric softeners, non-detergent based fabric care products, household cleaners and textile-care products.

11 Claims, No Drawings

STABILIZED BODY CARE PRODUCTS, HOUSEHOLD PRODUCTS, TEXTILES AND FABRICS

The present invention relates to the use of selected hindered nitroxyl, hydroxylamine and hydroxylamine salt compounds for the protection of body care products, household products, textiles and fabrics against the deleterious effects of light, heat and oxygen.

The stabilized compositions for example comprise dyes that are stabilized against color change.

BACKGROUND

Co-pending U.S. application Ser. No. 09/830,788, filed May 1, 2002 and Ser. No. 09/830,787, filed May 1, 2001 are aimed at the stabilization of body care and household products.

WO 01/07550 teaches the treatment of fabric with hindered amine stabilizers.

U.S. Pat. No. 6,254,724 teaches the stabilization of pulp and paper with hindered-amine based compounds.

DETAILED DISCLOSURE

The present invention pertains to a stabilized composition comprising
(a) a body care product, household product, textile or fabric and
(b) an effective stabilizing amount of at least one compound selected from the group consisting of
  (i) hindered nitroxyl compounds of formula (I),
  (ii) hindered hydroxylamine compounds of formula (II) and
  (iii) hindered hydroxylamine salt compounds of formula (III)

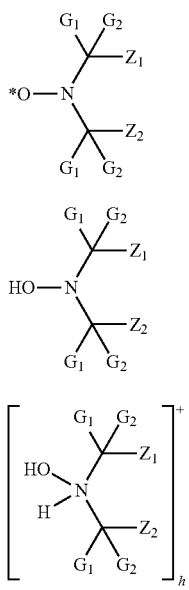

where
$G_1$ and $G_2$ are independently alkyl of 1 to 4 carbon atoms or are together pentamethylene,
$Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group, X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j.

For instance, X is chloride, bisulfite, bisulfate, sulfate, phosphate, nitrate, ascorbate, acetate, citrate or carboxylate of ethylenediaminetetraacetic acid or of diethylenetriaminepentaacetic acid; for instance X is bisulfate or citrate.

The hindered nitroxyl, hydroxylamine and hydroxylamine salt compounds of component (b) are for example of formulae A to EE and A* to EE*

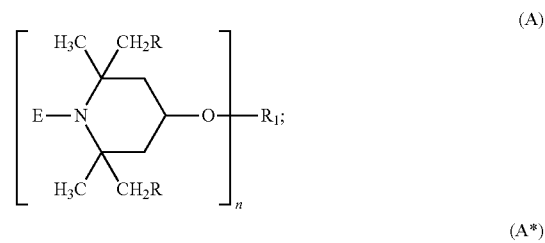

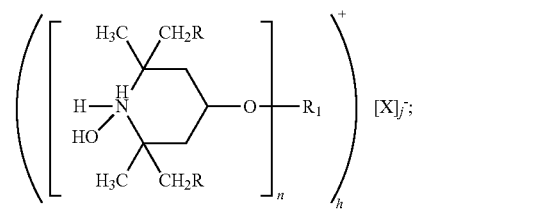

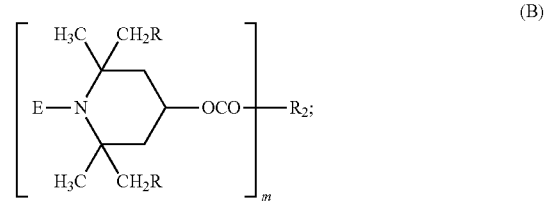

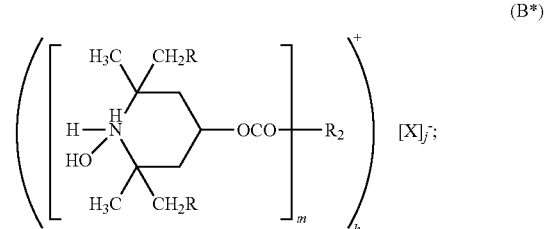

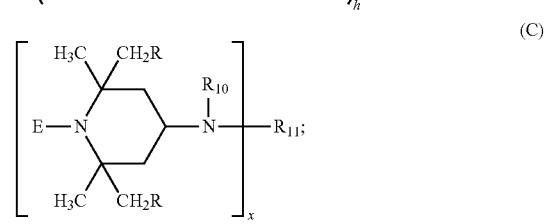

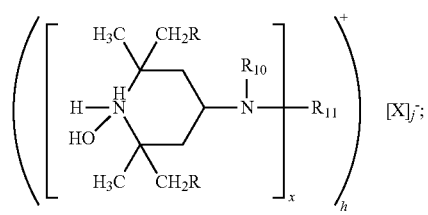
(C*)
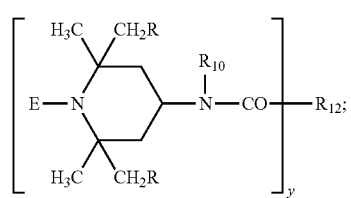
(D)
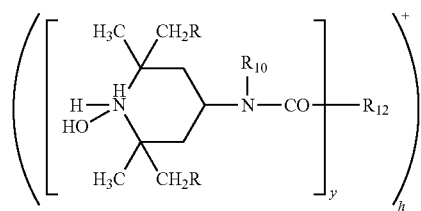
(D*)
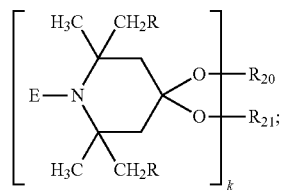
(E)
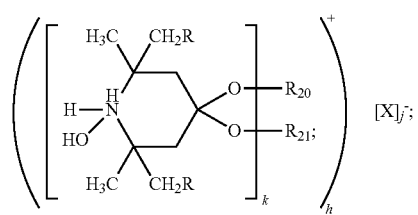
(E*)
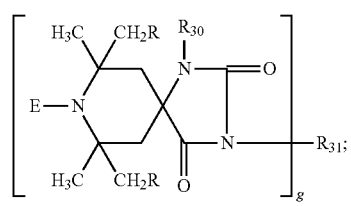
(F)
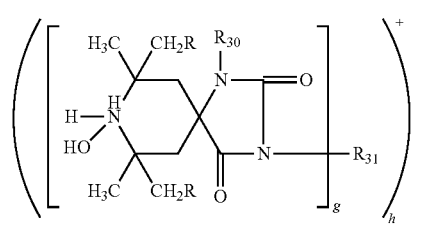
(F*)
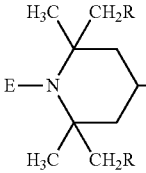
(G)
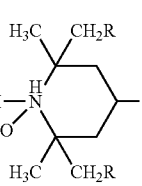
(G*)
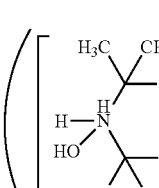
(H)
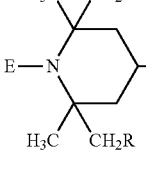
(H*)
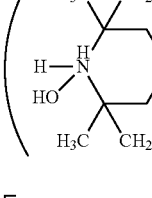
(I)
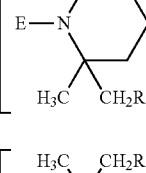
(I*)
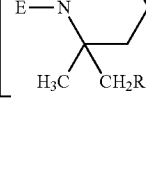
(J)
(J*)

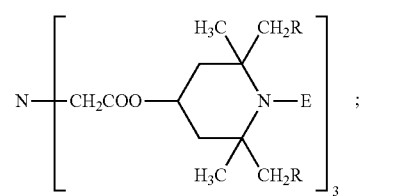 (K)
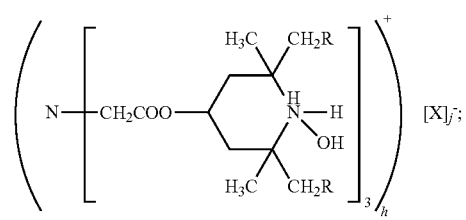 (K*)
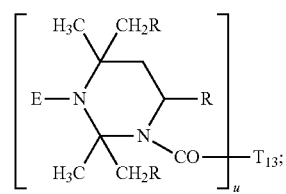 (L)
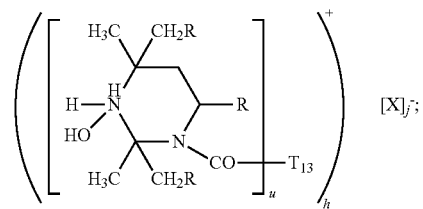 (L*)
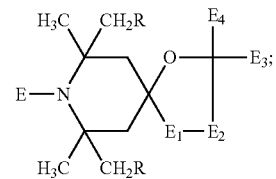 (M)
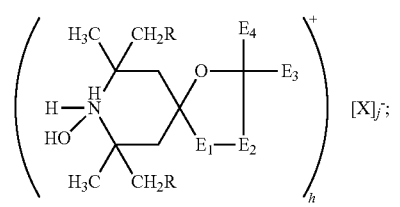 (M*)
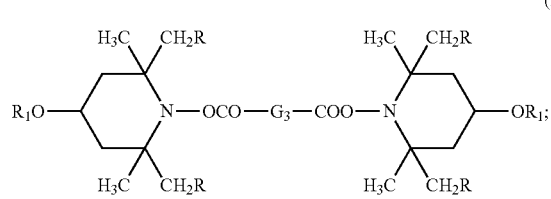 (N)
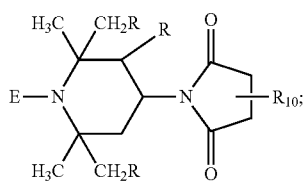 (O)
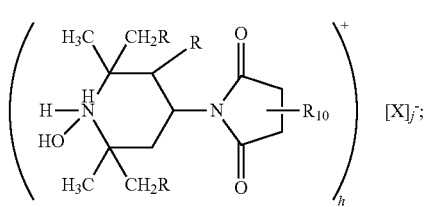 (O*)
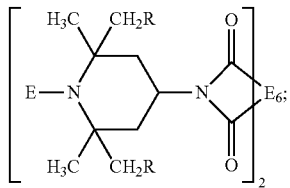 (P)
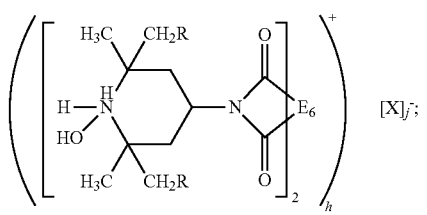 (P*)
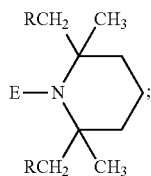 (Q)
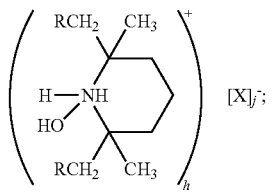 (Q*)
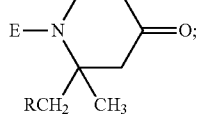 (R)
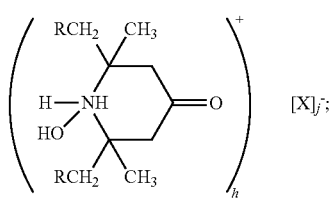 (R*)

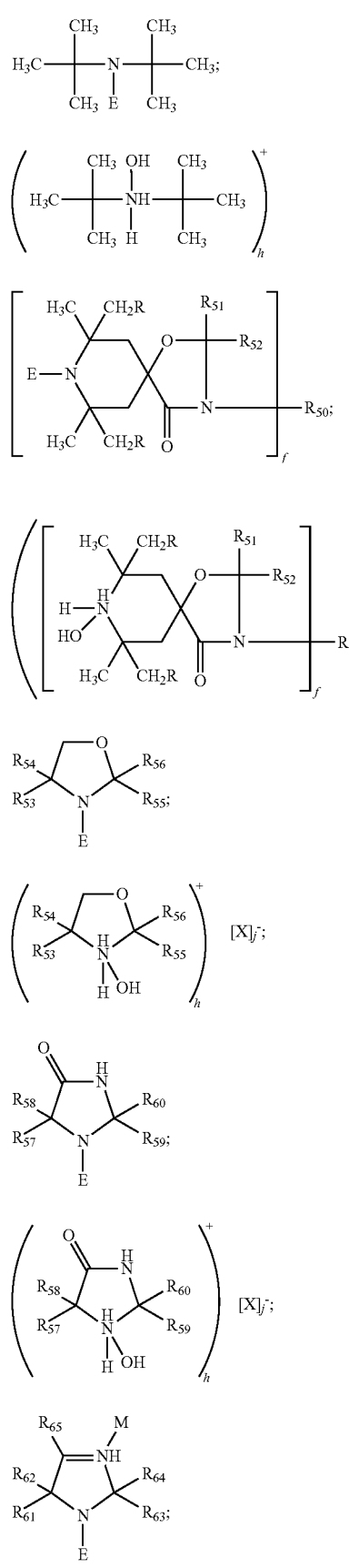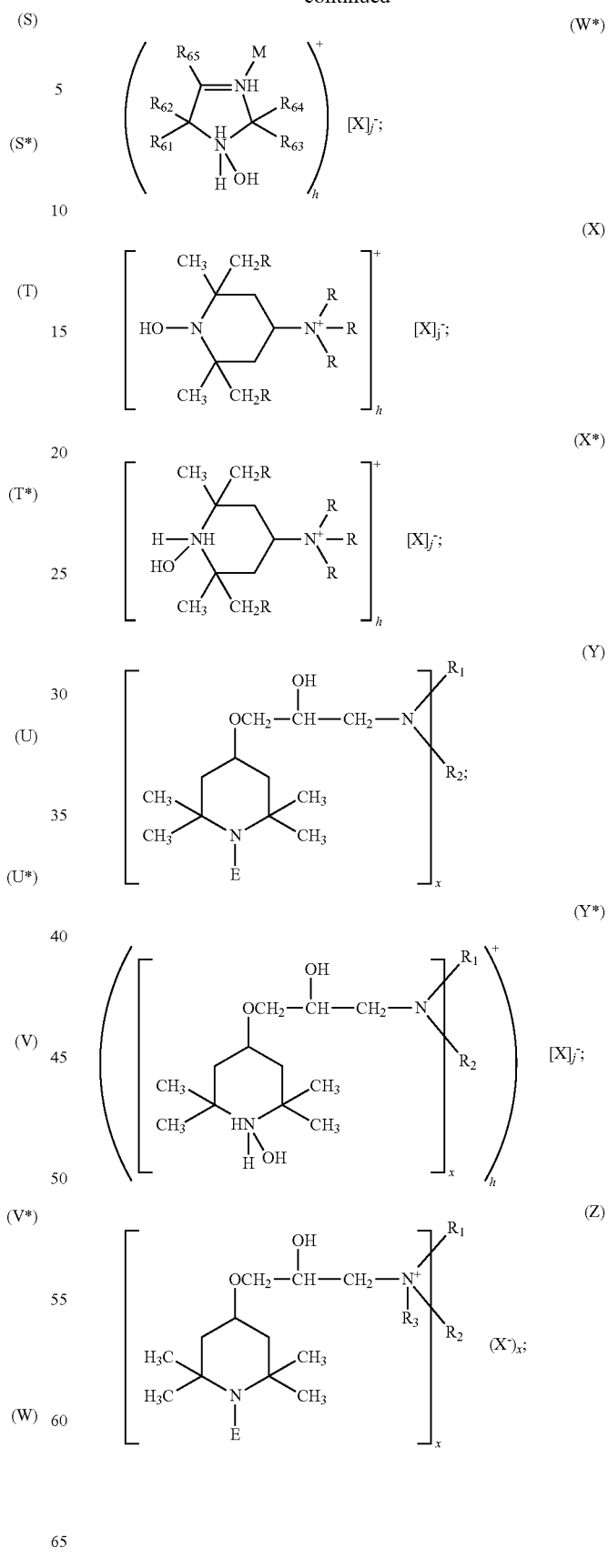

(Z*)
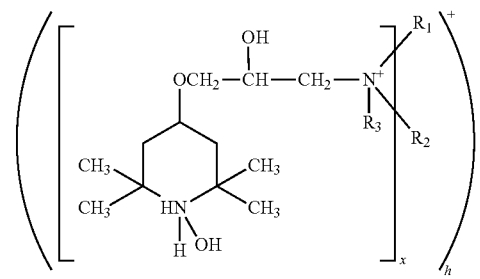
[X]ⱼ⁻;

(AA)
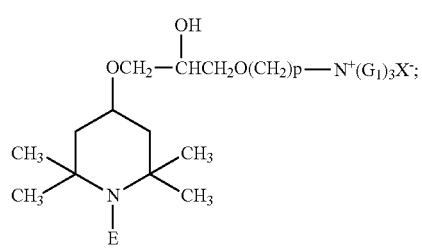

(AA*)
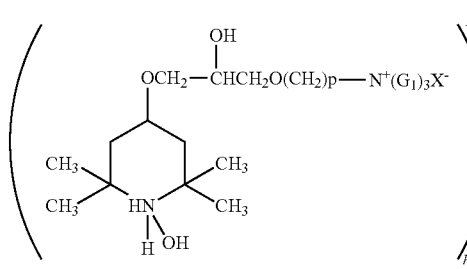
[X]ⱼ⁻;

(BB)
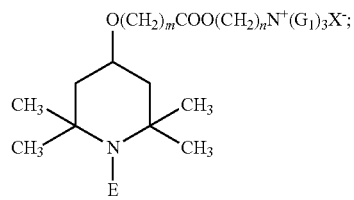

(BB*)
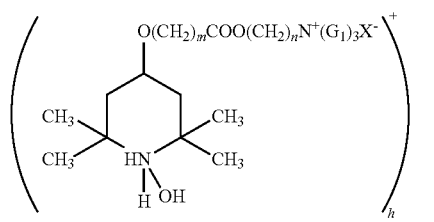
[X]ⱼ⁻;

(CC)
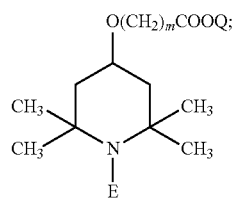

(CC*)
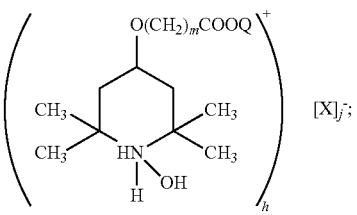
[X]ⱼ⁻;

(DD)
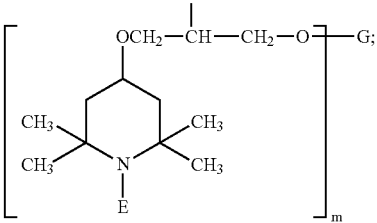

(DD*)
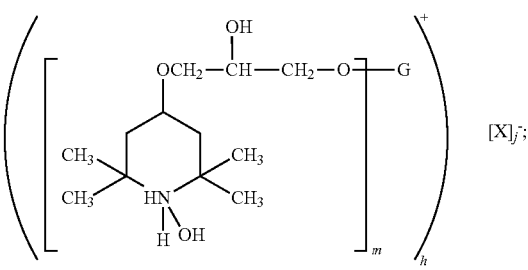
[X]ⱼ⁻;

(EE)
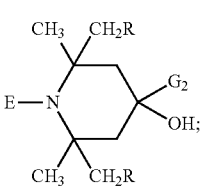

(EE*)
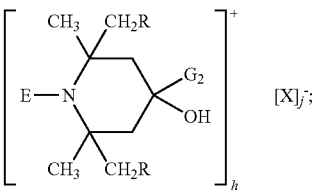
[X]ⱼ⁻;

wherein
E is oxyl or hydroxyl,
R is hydrogen or methyl,
in formula A and A*,
n is 1 or 2,
when n is 1,
$R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO⁻)$_n$M$^{n+}$ where n is 1-3 and M is a metal ion from the 1st, 2nd or 3rd group of the periodic table or is Zn, Cu, Ni or Co, or M is a group N'''⁺(R₂)₄ where $R_2$ is alkyl of 1 to 8 carbon atoms or benzyl, when n is 2,
R$_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula B and B*,
m is 1 to 4,
when m is 1,
R$_2$ is alkyl of 1 to 18 carbon atoms, alkyl of 3 to 18 carbon atoms interrupted by —COO—, or
R$_2$ is —CH$_2$(OCH$_2$CH$_2$)$_n$OCH$_3$ where n is 1 to 12, or
R$_2$ is cycloalkyl of 5 to 12 carbon atoms, aryl of 6 to 12 carbon atoms, or said aryl substituted by one to four alkyl groups of 1 to 4 carbon atoms, or
R$_2$ is —NHR$_3$ where R$_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or
R$_2$ is —N(R$_3$)$_2$ where R$_3$ is as defined above,
when m is 2,
R$_2$ is alkylene of 1 to 12 carbon atoms, alkenylene of 4 to 12 carbon atoms, xylylene, alkylene of 2 to 12 carbon atoms interrupted by —COO—, or R$_2$ is —CH$_2$(OCH$_2$CH$_2$)$_n$OCH$_2$— where n is 1 to 12, or
R$_2$ is cycloalkylene of 5 to 12 carbon atoms, aralkylene of 7 to 15 carbon atoms or arylene of 6 to 12 carbon atoms, or
R$_2$ is —NHR$_4$NH— where R$_4$ is alkylene of 2 to 18 carbon atoms, cycloalkylene of 5 to 12 carbon atoms, aralkylene of 8 to 15 carbon atoms or arylene of 6 to 12 carbon atoms, or
R$_2$ is —N(R$_3$)R$_4$N(R$_3$)— where R$_3$ and R$_4$ are as defined above, or
R$_2$ is —CO— or —NH—CO—NH—,
when m is 3,
R$_2$ is alkanetriyl of 3 to 8 carbon atoms or benzenetriyl, or
when m is 4,
R$_2$ is alkanetetrayl of 5 to 8 carbon atoms or benzenetetrayl,
in formula C and C*,
R$_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl,
x is 1 or 2,
when x is 1,
R$_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
R$_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^+$ where n is 1-3 and M is a metal ion from the 1st, 2nd or 3rd group of the periodic table or is Zn, Cu, Ni or Co, or M is a group N$^{n+}$ (R$_2$)$_4$ where R$_2$ is hydrogen, alkyl of 1 to 8 carbon atoms or benzyl, or
when x is 2,
R$_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula D and D*,
R$_{10}$ is as defined above,
y is 1 to 4, and
R$_{12}$ is defined as R$_2$ above
in formula E and E*,
k is 1 or 2,
when k is 1,
R$_{20}$ and R$_{21}$ are independently alkyl of 1 to 12 carbon atoms, alkenyl of 2 to 12 carbon atoms or aralkyl of 7 to 15 carbon atoms, or R$_{20}$ is also hydrogen, or
R$_{20}$ and R$_{21}$ together are alkylene of 2 to 8 carbon atoms or said alkylene substituted by hydroxyl, or are acyloxyalkylene of 4 to 22 carbon atoms, or
when k is 2,
R$_{20}$ and R$_{21}$ are together (—CH$_2$)$_2$C(CH$_2$—)$_2$,
in formula F and F*,
R$_{30}$ is hydrogen, alkyl of 1 to 18 carbon atoms, benzyl, glycidyl, or alkoxyalkyl of 2 to 6 carbon atoms,
g is 1 or 2,
when g is 1, R$_{31}$ is defined as R$_1$ above when n is 1,
when g is 2, R$_{31}$ is defined as R$_1$ above when n is 2,
in formula G and G*,
Q$_1$ is —NR$_{41}$— or —O—,
E$_1$ is alkylene of 1 to 3 carbon atoms, or E$_1$ is —CH$_2$—CH(R$_{42}$)—O— where R$_{42}$ is hydrogen, methyl or phenyl, or E$_1$ is —(CH$_2$)$_3$—NH— or E$_1$ is a direct bond,
R$_{40}$ is hydrogen or alkyl of 1 to 18 carbon atoms,
R$_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or R$_{41}$ is —CH$_2$—CH(R$_{42}$)—OH where R$_{42}$ is as defined above,
in formula H and H*,
p is 1 or 2,
T$_4$ is as defined for R$_{11}$ when x is 1 or 2,
M and Y are independently methylene or carbonyl, for instance M is methylene and Y is carbonyl,
in formula I and I*,
this formula denotes a recurring structural unit of a polymer where T$_1$ is ethylene or 1,2-propylene or is the repeating structural unit derived from an alpha-olefin copolymer with an alkyl acrylate or methacrylate, and where
q is 2 to 100,
Q$_1$ is —N(R$_{41}$)— or —O— where R$_{41}$ is as defined above,
in formula J and J*,
r is 1 or 2,
T$_7$ is as defined for R$_1$ when n is 1 or 2 in formula A,
for example T$_7$ is octamethylene when r is 2,
in formula L and L*,
u is 1 or 2,
T$_{13}$ is as defined for R$_1$ when n is 1 or 2 in formula A, with the proviso that T$_{13}$ is not hydrogen when u is 1,
in formula M and M*,
E$_1$ and E$_2$, being different, each are —CO— or —N(E$_5$)- where E$_5$ is hydrogen, alkyl of 1 to 12 carbon atoms or alkoxycarbonylalkyl of 4 to 22 carbon atoms, for instance E$_1$ is —CO— and E$_2$ is —N(E$_5$)-,
E$_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms,
E$_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, for example methyl, in formula N,
$R_1$ is as defined for $R_1$ in formula A when n is 1,
$G_3$ is a direct bond, alkylene of 1 to 12 carbon atoms, phenylene or —NH-$G_1$-NH— where $G_1$ is alkylene of 1 to 12 carbon atoms, in formula O and O*,
$R_{10}$ is as defined for $R_{10}$ in formula C, in formula P and P*,
$E_6$ is an aliphatic or aromatic tetravalent radical, for example neopentanetetrayl or benzenetetrayl, in formula T and T*,
$R_{51}$ is hydrogen, alkyl of 1 to 18 carbon atoms, cycloalkyl of 5 to 12 carbon atoms, or aryl of 6 to 10 carbon atoms,
$R_{52}$ is hydrogen or alkyl of 1 to 18 carbon atoms, or
$R_{51}$ and $R_{52}$ together of alkylene of 4 to 8 carbon atoms,
f is 1 or 2,
when f is 1,
$R_{50}$ is as defined for $R_{11}$ in formula C when x is 1, or $R_{50}$ is —$(CH_2)_z COOR_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —$N(R_{55})_4$ where $R_{55}$ is hydrogen, alkyl of 1 to 12 carbon atoms or benzyl,
when f is 2, $R_{50}$ is as defined for $R_{11}$ in formula C when x is 2, in formula U and U*,
$R_{53}$, $R_{54}$, $R_{55}$ and $R_{56}$ are independently alkyl of 1 to 4 carbon atoms or are together pentamethylene.

in formula V and V*,
$R_{57}$, $R_{58}$, $R_{59}$ and $R_{60}$ are independently alkyl of 1 to 4 carbon atoms or are together pentamethylene.

in formula W and W*,
$R_{61}$, $R_{62}$, $R_{63}$ and $R_{64}$ are independently alkyl of 1 to 4 carbon atoms or are together pentamethylene,
$R_{65}$ is alkyl of 1 to 5 carbon atoms,
M is hydrogen or oxygen, wherein in formulas X to CC and X* to CC*
n is 2 to 3,
$G_1$ is hydrogen, methyl, ethyl, butyl or benzyl,
m is 1 to 4,
x is 1 to 4,
when x is 1,
$R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen,
or $R_1$ and $R_2$ are together tetramethylene, pentamethylene, hexamethylene or 3-oxapentamethylene,
when x is 2,
$R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group,
$R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_k O[(CH_2)_k O]_h (CH_2)_k$— where k is 2 to 4 and h is 1 to 40, or
$R_1$ and $R_2$ together with the two N atoms to which they are attached are piperazin-1,4-diyl,
when x is 3,
$R_1$ is hydrogen
$R_2$ is alkylene of 4 to 8 carbon atoms interrupted by one nitrogen atom,
when x is 4,
$R_1$ is hydrogen,
$R_2$ is alkylene of 6 to 12 carbon atoms interrupted by two nitrogen atoms,
$R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group,
P is 2 or 3, and
Q is an alkali metal salt, ammonium or $N^+(G_1)_4$ in formula DD and DD*
m is 2 or 3,
when m is 2,
G is —$(CH_2 CHR—O)_r CH_2 CHR$—, where r is 0 to 3, and R is hydrogen or methyl, and
when m is 3,
G is glyceryl, in formula EE and EE*
$G_2$ is —CN, —$CONH_2$ or —$COOG_3$ where $G_3$ is hydrogen, alkyl of 1 to 18 carbon atoms or phenyl,
X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j.

For example, the compounds of component (b) are those of formulas A, A*, B, B*, C, C*, D, D*, Q, Q*, R, R*, S, S*, X, X, Y, Y*, Z and Z*,
R is hydrogen,
in formula A and A*
n is 1 or 2,
when n is 1,
$R_1$ is hydrogen, alkyl of 1 to 6 carbon atoms, alkenyl of 2-6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen or alkyl of 1 to 4 carbon atoms,
when n is 2,
$R_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups,
in formula B and B*
m is 1 or 2 when m is 1,
R₂ is alkyl of 1 to 4 carbon atoms or R₂ is CH₂(OCH₂CH₂)ₙOCH₃ where n is 1 to 12, or
R₂ is phenyl, or said phenyl substituted by one to three methyl groups,
R₂ is —NHR₃ where R₃ is alkyl of 1 to 4 carbon atoms or phenyl, or said phenyl substituted by one or two methyl groups,
when m is 2,
R₂ is alkylene of 1 to 8 carbon atoms, alkenylene of 4 to 8 carbon atoms, or R₂ is —CH₂(OCH₂CH₂)ₙOCH₂— where n is 1 to 12,
R₂ is NHR₄NH where R₄ is of 2 to 6 carbon atoms, aralkylene of 8 to 15 carbon atoms or arylene of 6 to 12 carbon atoms,
R₂ is —CO— or —NHCONH,
in formula C and C*,
R₁₀ is hydrogen or, alkanoyl of 1 to 3 carbon atoms,
x is 1 or 2,
when x is 1,
R₁₁ is hydrogen, alkyl of 1 to 6 carbon atoms or glycidyl,
R₁₁ is alkyl of 1 to 4 carbon atoms substituted by a carboxy group or by COOZ where Z is hydrogen or alkyl of 1 to 4 carbon atoms,
when x is 2,
R₁₁ is alkylene of 1 to 6 carbon atoms,
in formula D and D*,
R₁₀ is hydrogen,
y is 1 or 2,
R₁₂ is defined as R₂ above,
in formula Y, Y*, Z and Z*,
x is 1 or 2,
when x is 1,
R₁ and R₂ are independently alkyl of 1 to 4 carbon atoms, or R₁ and R₂ are together tetramethylene, or pentamethylene,
R₂ is hydrogen or alkyl of 1 to 4 carbon atoms, said alkyl group substituted by a hydroxyl group,
when x is 2,
R₁ is hydrogen, alkyl of 1 to 4 carbon atoms, said alkyl substituted by a hydroxyl group,
R₂ is alkylene of 2 to 6 carbon atoms,
R₃ is as defined above.
For instance, the compounds of component (b) are those of formulas A, A*, B, B*, C, C*, D, D*, Q, Q*, R and R*,
R is hydrogen,
in formula A and A*,
h is 1,
R₁ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
R₁ is alkyl of 1 to 4 carbon atoms substituted by —COOZ where Z is hydrogen or alkyl of 1 to 4 carbon atoms,
in formula B and B*,
m is 1 or 2,
R₂ is alkyl of 1 to 4 carbon atoms or N is CH₂(OCH₂CH₂)ₙOCH₃ where n is 1 to 4,
when m is 2,
R₂ is alkylene of 1 to 8 carbon atoms,
in formula C and C*,
R₁₀ is hydrogen or alkanoyl of 1 or 2 carbon atoms,
x is 1 or 2,
when x is 1,
R₁₁ is hydrogen, alkyl of 1 to 4 carbon atoms or glycidyl, R₁₁ is alkyl of 1 to 4 carbon atoms substituted by COOZ where Z is hydrogen or alkyl of 1 to 4 carbon atoms,
when x is 2,
R₁₁ is alkylene of 1 to 6 carbon atoms,
in formula D and D*,
R₁₀ is hydrogen,
y is 1 or 2,
R₁₂ is defined as R₂ above.

For instance, the hindered nitroxyl, hydroxylamine and hydroxylamine salt compounds of component (b) are selected from bis(1-oxyl-2,2-6-6-tetramethylpiperidinyl) sebacate; bis(1-hydroxy-2,2-6-6-tetramethylpiperidin-4-yl) sebacate; 1-hydroxy-2,2-6-6-tetramethyl-4-acetoxypiperidinium citrate; 1-oxyl-2,2,6,6-tetramethyl-4-acetamidopiperidine; 1-hydroxy-2,2,6,6-tetramethyl-4-acetamidopiperidine; 1-hydroxy-2,2,6,6-tetramethyl-4-acetamidopiperidinium bisulfate; 1-oxyl-2,2,6,6-tetramethyl-4-oxo-piperidine; 1-hydroxy-2,2,6,6-tetramethyl-4-oxo-piperidine; 1-hydroxy-2,2,6,6-tetramethyl-4-oxo-piperidinium acetate; 1-oxyl-2,2,6,6-tetramethyl-4methoxy-piperidine; 1-hydroxy-2,2,6,6-tetramethyl-4-methoxy-piperidine; 1-hydroxy-2,2,6,6-tetramethyl-4-methoxy-piperidinium acetate; 1-oxyl-2,2,6,6-tetraethyl-4-acetoxypiperidine; 1-hydroxy-2,2,6,6-tetramethyl-4-acetoxypiperidine; 1-oxyl-2,2,6,6-tetramethyl-4-propoxy-piperidine; 1-hydroxy-2,2,6,6-tetramethyl-4-propoxy-piperidinium acetate; 1-hydroxy-2,2,6,6-tetramethyl-4-propoxy-piperidine; 1-oxyl-2,2,6,6-tetramethyl-4-(2-hydroxy-4-oxapentoxy)piperidine; 1-hydroxy-2,2,6,6-tetramethyl-4-(2-hydroxy-4-oxapentoxy)piperidinium acetate; 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxopiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium) diethylenetriaminepentaacetate; penta(1-hydroxy-2,2,6,6-tetramethyl-4-acetamidopiperidinium) diethylenetriaminepentaacetate; penta(1-hydroxy-2,2,6,6-tetramethyl-4-oxopiperidinium) diethylenetriaminepentaacetate; tri(1-hydroxy-2,2,6,6-tetramethyl-4-hydroxypiperidinium) nitrilotriacetate; tri(1-hydroxy-2,2,6,6-tetramethyl-4-acetamidopiperidinium) nitrilotriacetate; tri(1-hydroxy-2,2,6,6-tetramethyl-4-oxopiperidinium) nitrilotriacetate; penta(1-hydroxy-2,2,6,6-tetramethyl-4hydroxypiperidinium) diethylenetriaminepentamethylenephosphonate; penta(1-hydroxy-2,2,6,6-tetramethyl-4-acetamidopiperidinium) diethylenetriaminepentamethylenephosphonate; and penta(1-hydroxy-2,2,6,6-tetramethyl-4-oxopiperidinium) diethylenetriaminepentamethylenephosphonate.

For example, the hindered nitroxyl, hydroxylamine and hydroxylamine salt compounds of component (b) are selected from 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxpiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6tetramethyl-4-hydroxypiperidinium) citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium) diethylenetriaminepentaacetate; penta(1-hydroxy-2,2,6,6-tetramethyl-4-acetamidopiperidinium) diethylenetriaminepentaacetate; and penta(1-hydroxy-2,2,6,6-tetramethyl-4-oxopiperidinium) diethylenetriaminepentaacetate.

For example, the compounds of component (b) are selected from 1-hydroxy-2,2,6,6-tetramethyl-4hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; 1-hydroxy-2,2,6,6-tetramethyl-4-hydroxypiperidinium DTPA; bis(1-hydroxy-2,2,6,6-tetramethyl-4-hydroxypiperidinium) DTPA; tris(1-hydroxy-2,2,6,6-tetramethyl-4-hydroxypiperidinium) DTPA; tetrakis(1-hydroxy-2,2,6,6-tetramethyl-4-hydroxypiperidinium) DTPA; pentakis(1-hydroxy-2,2,6,6-tetramethyl-4-hydroxypiperidinium) DTPA; 1-hydroxy-2,2,6,6-tetramethyl-4-hydroxypiperidinium EDTA; bis(1-hydroxy-2,2,6,6-tetramethyl-4-hydroxypiperidinium) EDTA; tris(1-hydroxy-2,2,6,6-tetramethyl-4-hydroxypiperidinium) EDTA; tetrakis(1-hydroxy-2,2,6,6-tetra-methyl-4-hydroxypiperidinium) EDTA; 1-hydroxy-2,2,6,6-tetramethyl-4-oxo-piperidinium citrate; bis(1-hydroxy-2,2,6,6-tetramethyl-4-oxo-piperidinium) citrate; tris(1-hydroxy-2,2,6,6-tetramethyl-4-oxopiperidinium) citrate; 1-hydroxy-2,2,6,6-tetramethyl-4-oxopiperidinium DTPA; bis(1-hydroxy-2,2,6,6-tetramethyl-4-oxo-piperidinium) DTPA; tris(1-hydroxy-2,2,6,6-tetramethyl-4-oxo-piperidinium) DTPA; tetrakis(1-hydroxy-2,2,6,6-tetramethyl-4-oxo-piperidinium) DTPA; pentakis(1-hydroxy-2,2,6,6-tetramethyl-4-oxo-piperidinium) DTPA; 1-hydroxy-2,2,6,6-tetramethyl-4-oxo-piperidinium EDTA; bis(1-hydroxy-2,2,6,6-tetramethyl-4-oxo-piperidinium) EDTA; tris(1-hydroxy-2,2,6,6-tetramethyl-4-oxo-piperidinium) EDTA; tetrakis(1-hydroxy-2,2,6,6-tetramethyl-4-oxo-piperidinium) EDTA; 1-hydroxy-2,2,6,6-tetra-methyl-4-acetamidopiperidinium citrate; bis(1-hydroxy-2,2,6,6-tetramethyl-4-acetamidopiperidinium) citrate; tris(1-hydroxy-2,2,6,6-tetramethyl-4-acetamidopiperidinium) citrate; 1-hydroxy-2,2,6,6-tetramethyl-4-acetamidopiperidinium DTPA; bis(1-hydroxy-2,2,6,6-tetramethyl-4-acetamidopiperidinium) DTPA; tris(1-hydroxy-2,2,6,6-tetramethyl-4-acetamidopiperidinium) DTPA; tetrakis(1-hydroxy-2,2,6,6-tetramethyl-4-acetamidopiperidinium) DTPA; pentakis(1-hydroxy-2,2,6,6-tetramethyl-4-acetamidopiperidinium) DTPA; 1hydroxy-2,2,6,6-tetramethyl-4-acetamidopiperidinium EDTA; bis(1-hydroxy-2,2,6,6-tetramethyl-4-acetamidopiperidinium) EDTA; tris(1-hydroxy-2,2,6,6-tetramethyl-4-acetamidopiperidinium) EDTA; tetrakis(1-hydroxy-2,2,6,6-tetramethyl-4-hydroxypiperidinium) EDTA; 1-hydroxy-2,2,6,6-tetramethyl-4-acetoxypiperidinium citrate; bis(1-hydroxy-2,2,6,6-tetramethyl-4-acetoxypiperidinium) citrate; tris(1-hydroxy-2,2,6,6-tetramethyl-4-acetoxypiperidinium) citrate; 1-hydroxy-2,2,6,6-tetramethyl-4-acetoxypiperidinium DTPA; bis(1-hydroxy-2,2,6,6-tetramethyl-4-acetoxypiperidinium) DTPA; tris(1-hydroxy-2,2,6,6-tetramethyl-4-acetoxypiperidinium) DTPA; tetrakis(1-hydroxy-2,2,6,6-tetramethyl-4-acetoxypiperidinium) DTPA; pentakis(1-hydroxy-2,2,6,6-tetramethyl-4-acetoxypiperidinium) DTPA; 1-hydroxy-2,2,6,6-tetramethyl-4-acetoxypiperidinium EDTA; bis(1-hydroxy-2,2,6,6-tetramethyl-4-acetoxypiperidinium) EDTA; tris(1-hydroxy-2,2,6,6-tetramethyl-4-acetoxypiperidinium) EDTA and tetrakis(1-hydroxy-2,2,6,6-tetramethyl-4-acetoxypiperidinium) EDTA.

The above named counter-ions are ethylenediaminetetraacetic acid (EDTA), diethylenetriaminepentaacetic acid (DTPA), hydroxyethylethylenediaminetriacetic acid (HEDTA), nitrilotriacetic acid (NTA) or diethylenetriaminepentamethylenephosphonic acid (DTPMPA).

The present compositions may comprise further traditional additives, for example ultraviolet (UV) light absorbers and antioxidants.

Accordingly, the present invention further pertains to a stabilized composition comprising
(a) a body care product, household product, textile or fabric,
(b) an effective stabilizing amount of at least one compound selected from the group consisting of
    (i) hindered nitroxyl compounds of formula (I),
    (ii) hindered hydroxylamine compounds of formula (II) and
    (iii) hindered hydroxylamine salt compounds of formula (Ill) and
(c) at least one compound selected from the group consisting of the ultraviolet light absorbers, antioxidants, tocopherol, tocopherol acetate, hindered amine light stabilizers, complex formers, optical brighteners, surfactants, and polyorganosiloxanes.

The additional additives of present component (c) are for example those disclosed in co-pending U.S. application Ser. No. 09/830,788, filed May 1, 2001 and Ser. No. 09/830,787, filed May 1, 2001. The disclosures of these co-pending applications are hereby incorporated by reference.

The UV absorbers are for example selected from group consisting of the 2H-benzotriazoles, the s-triazines, the benzophenones, the α-cyanoacrylates, the oxanilides, the benzocazinones, the benzoates and the α-alkyl cinnamates.

The UV absorbers are for example 2,4,6-tris(2-hydroxy-4-octyloxyphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)phenyl]-4,6-bis(2,4-dimethylphenyl)-1,3,5-triazine; 2-[2-hydroxy-4-2-hydroxy-3-tridecyloxypropyloxy)-phenyl]-4,6-bis(2,4-dimethylphenyl)-1,3,5-triazine; 5-chloro-2-(2-hydroxy-3,5-di-tert-butylphenyl)-2H-benzotriazole; 2-(2-hydroxy-3-dodecyl-5-methylphenyl)-2H-benzotriazole; 5-chloro-2-(2-hydroxy-3-tert-butyl-5-methylphenyl)-2H-benzotriazole; bis-(3-(2H-benzotriazol-2-yl)-2-hydroxy-5-tert-octyl)methane; 2-(2-hydroxy-3,5-di-tert-butylphenyl)-2H-benzotriazole; 2-(2-hydroxy-3,5-di-tert-amylphenyl)-2H-benzotriazole; 2-(2-hydroxy-3,5-di-αcumylphenyl)-2H-benzotriazole; 2-(2-hydroxy-3α-cumyl-5-tert-octylphenyl)-2H-benzotriazole; 2-(2-hydroxy-5-tert-octylphenyl)-2H-benzotriazole; 3-(2H-benzotriazol-2-yl)-4-hydroxy-5-(1-methylpropyl)-benzenesulfonic acid monosodium salt; 3-tert-butyl-4-hydroxy-5-(2H-benzotriazol-2-yl)-hydrocinnamic acid and sodium salt; 12-hydroxy-3,6,9-trioxadodecyl 3-tert-butyl-4-hydroxy-5-(2H-benzotriazol-2-yl)-hydrocinnamate; octyl 3-tert-butyl-4-hydroxy-5-(2H-benzotriazol-2-yl)-hydrocinnamate; 4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers); 4,6-bis(2,4-dimethylphenyl)-2-

(4-octyloxy-2-hydroxyphenyl)-s-triazine; 2,4-dihydroxybenzophenone; 2,2'-dihydroxy-4,4'-dimethoxy-5,5'-disulfobenzophenone, disodium salt; 2-hydroxyoctyloxybenzophenone; 2-hydroxy-4-dodecyloxybenzophenone; 2,4-dihydroxybenzophenone; 2,2',4,4'-tetrahydroxybenzophenone; 4-aminobenzoic acid; 2,3-dihydroxypropyl-4-aminobenzoic acid; 3-(4-imidazolyl)acrylic acid; 2-phenyl-5-benzimidazole sulfonic acid; N,N,N-trimethyl-α-(2-oxo-3-bornylidene)-p-toluidinium methyl sulfate; 5-benzoyl-4-hydroxy-2-methoxybenzenesulfonic acid, sodium salt; 3-(4-benzoyl-3-hydroxyphenoxy)-2-hydroxy-N,N,N-trimethyl-1-propanaminium chloride; 3-[4-(2H-benzotriazol-2-yl)-3-hydroxyphenoxy]-2-hydroxy-N,N,N-trimethyl-1-propanaminium, chloride; 2-(2-hydroxy-5-methylphenyl)-2H-benzotriazole; and 2,2'-dihydroxy-4,4'-dimethoxybenzophenone (Uvinule 3049).

For instance, suitable UV absorbers are selected from 3-(2H-benzotriazol-2-yl)-4hydroxy-5-(1-methylpropyl)-benzenesulfonic acid monosodium salt; 3-tert-butyl-4-hydroxy-5(2H-benzotriazol-2-yl)-hydrocinnamic acid and sodium salt; 2-(2-hydroxy-3,5-di-tert-butylphenyl)-2H-benzotriazole; 2-(2-hydroxy-3,5-di-tert-amylphenyl)-2H-benzotriazole; 4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers); 12-hydroxy-3,6,9-trioxadodecyl 3-tert-butylhydroxy-5-(2H-benzotriazol-2-yl)-hydrocinnamate; 2,4-dihydroxybenzophenone; 2,2'-dihydroxy-4,4'-dimethoxy-5,5'-disulfobenzophenone, disodium salt; 2,2',4,4'-tetrahydroxybenzophenone; 3-(4-benzoyl-3-hydroxyphenoxy)-2-hydroxy-N,N,N-trimethyl-1-propanaminium chloride; 3-[4(2H-benzotriazol-2-yl)-3-hydroxyphenoxy]-2-hydroxy-N,N,N-trimethyl-1-propanaminium, chloride; 5-benzoyl-4-hydroxy-2-methoxy-benzenesulfonic acid, sodium salt; and 2-(2-hydroxy-3α-cumyl-5-tert-octylphenyl)-2H-benzotriazole.

Additional suitable antioxidants are for example selected from the hindered phenolic and benzofuranone stabilizers.

Suitable antioxidants are for example selected from the group consisting of

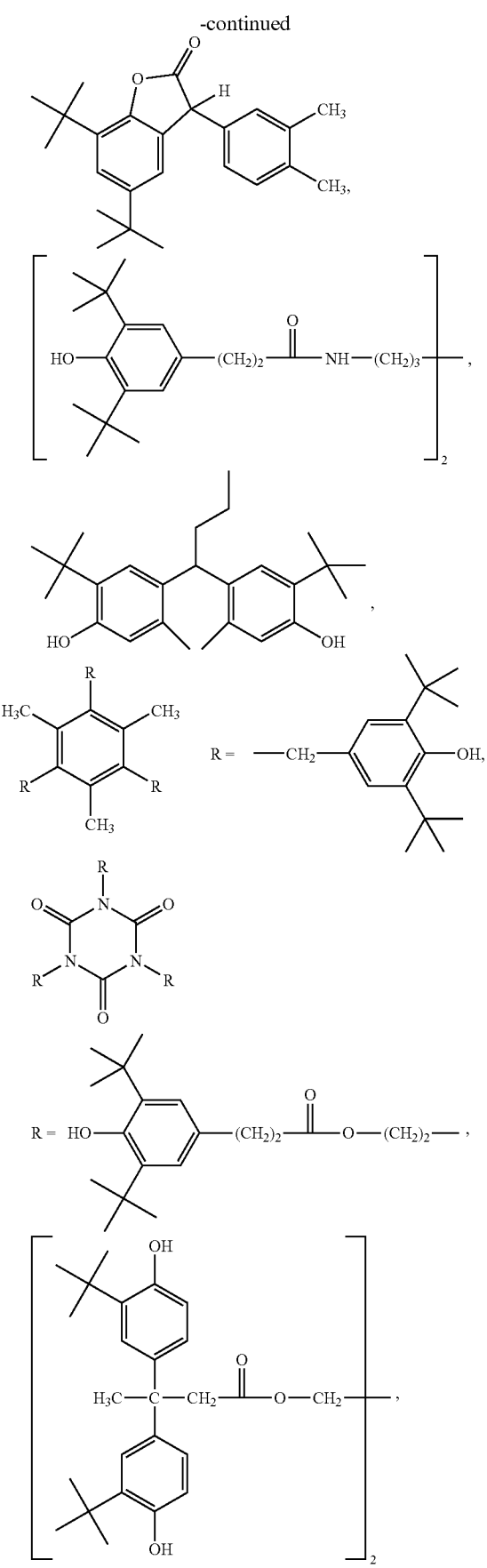

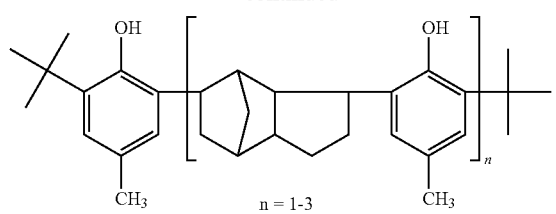
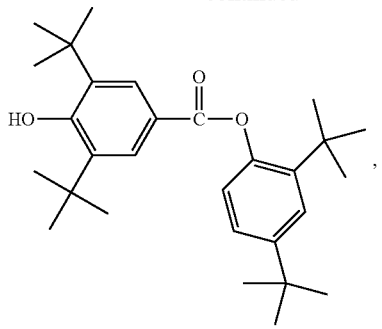
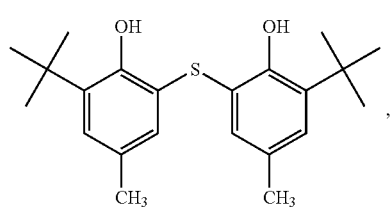
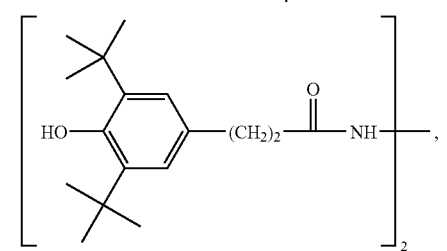
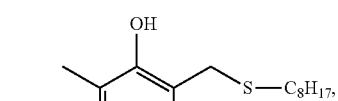
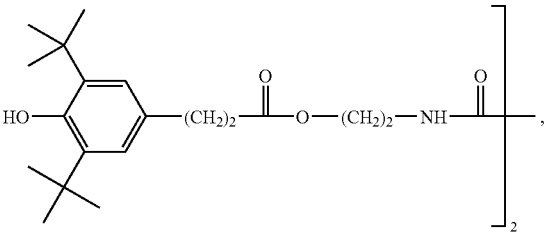
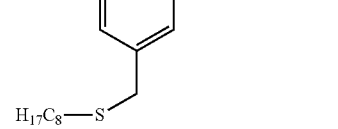
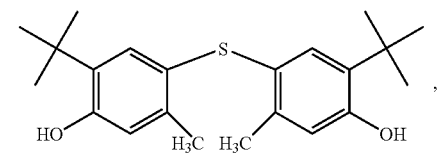
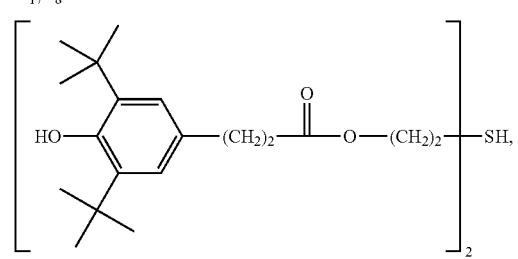
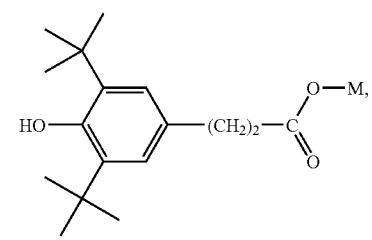
M = H, ammonium, alkali
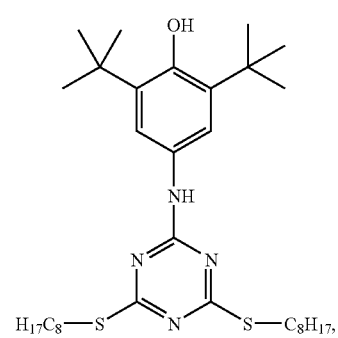
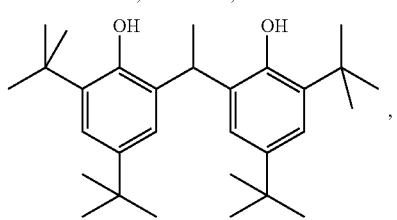
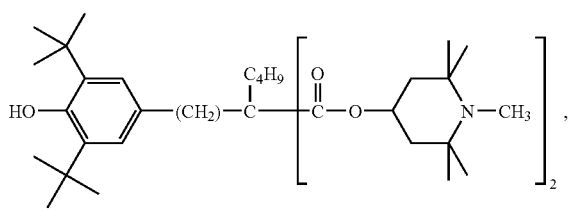
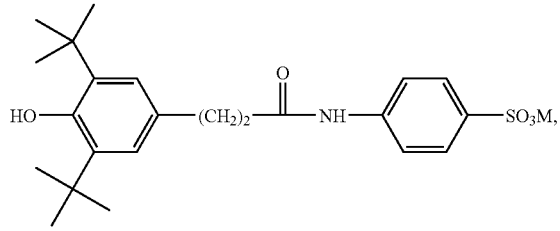
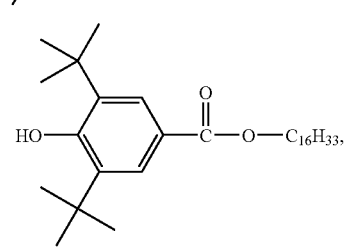
M = H, Na

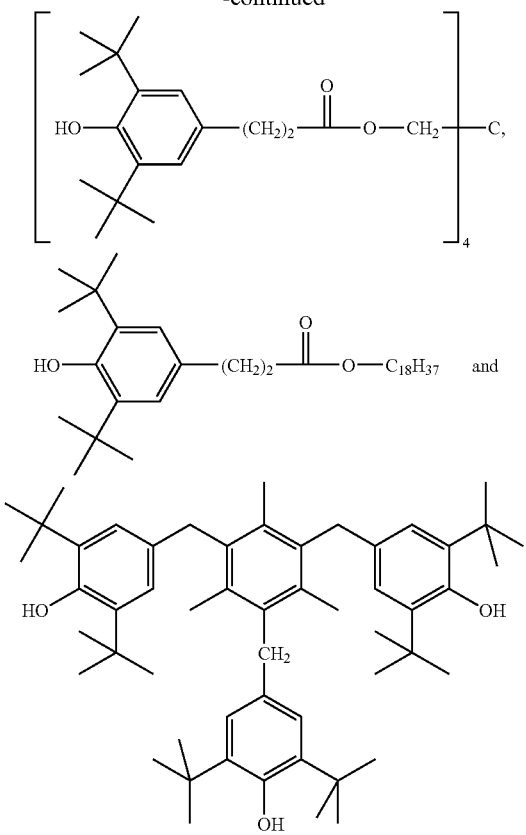

The hindered amine light stabilizers (HALS) of component (c) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, n-butyl-3,5-di-tert-butyl-4-hydroxybenzyl malonic acid-bis(1,2,2,6,6-pentamethylpiperidyl)ester, the condensate of 1-hydroxyethyl-2,2,6,6tetramethyl-4-hydroxypiperidine and succinic acid, the condensate of N,N'-bis(2,2,6,6-tetramethyl-4-piperidyl)hexamethylenediamine and 4tert-octylamino-2,6-dichloro-1,3,5-s-triazine, tris(2,2,6,6-tetramethyl-4-piperidyl)nitrilotriacetate, tetrakis(2,2,6,6-tetramethyl-4piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro-[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-di-aza-4-oxo-spiro[4,5]decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]-decane-2,4-dione,

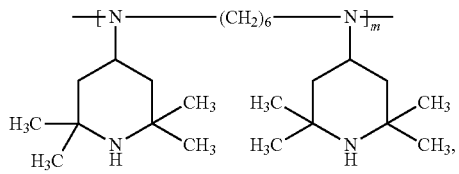

wherein m is a value from 5-50,

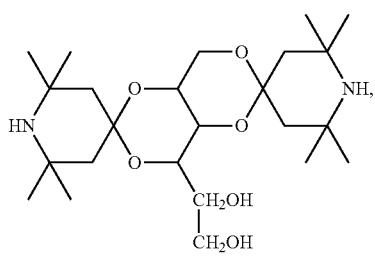

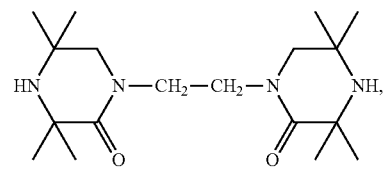

-continued

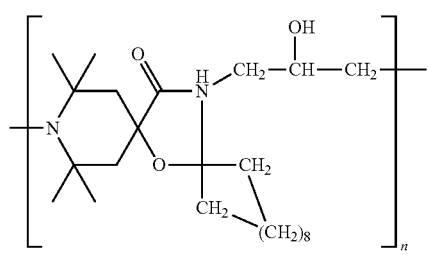

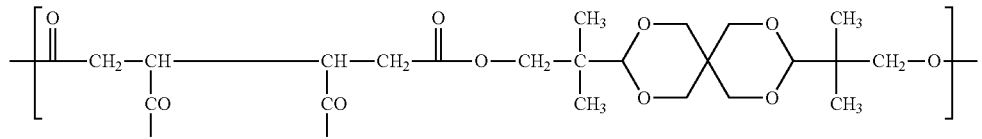

, and

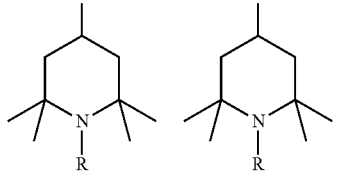

where R = H or CH$_3$

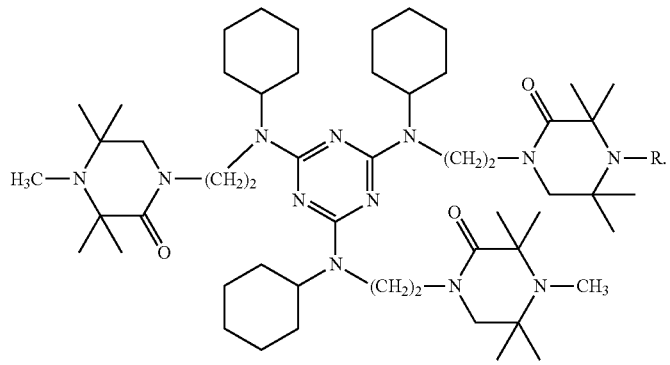

where R = H or CH$_3$

The complex formers of component (c) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers are for example selected from the group consisting of ethylenediaminetetracetic acid (EDTA), nitrilotriacetic acid (NTA), □-alaninediacetic acid (EDETA) or ethylenediaminedisuccinic acid (EDDS)

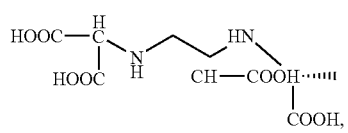

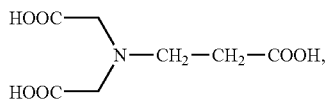

aminetrimethylenephosphoric acid (ATMP) conforming to formula

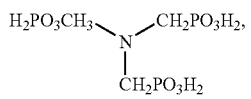

serinediacetic acid (SDA) conforming to formula

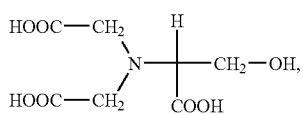

asparaginediacetic acid conforming to formula

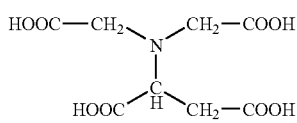

and methylglycinediacetic acid (MGDA) conforming to formula

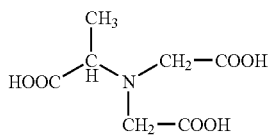

The present stabilizer systems are particularly suitable for stabilizing body care products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present body care products can be in the form of creams, ointments, pastes, foams, gels, lotions, powders, make-ups, sprays, sticks or aerosols. The present stabilizer systems may be present in the oil phase or in the aqueous or aqueous/alcoholic phase.

The additives of component (b) are present, for example, in the body care and household products in a concentration of about 5 to about 10000 ppm, based on the total formulation, for example from about 10 to about 5000 ppm, for example from about 100 to about 1000 ppm. For example the additives of component (b) are present in the body care and household products in a concentration of about 5, 10, 15, 20, 25, 35, 40, 45 or 50 ppm, based on the total formulation. For example, the additives of component (b) are present from about 5 to about 1000 ppm in the formulations (compositions) of this invention.

Laundry detergents, fabric softeners or other products, from which the additives of component (b) are intended for deposition onto fabrics with use, are considered household products of this invention, and the above concentration levels also pertain thereto. The present additives of component (b) are effective at stabilizing the laundry detergents and fabric softeners, as well as the fabrics treated therewith.

Creams are oil-in-water emulsions containing more than 50% water. The oil-containing base used therein is usually mainly fatty alcohols, for example lauryl, cetyl or stearyl alcohol, fatty acids, for example palmitic or stearic acid, liquid to solid waxes, for example isopropyl-myristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty add ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, for instance not more than 20 to 50%, of water or of an aqueous phase. The oil-containing phase contains predominantly hydrocarbons, such as paraffin oil and/or solid paraffin which for instance contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty add triglycerides or, for instance, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum Arabic and polyacrylate thickener systems. The gels for example additionally contain polyalcohols, such as propylene glycol or glycerol as moisturisers and wetting agents, such as polyoxyethylenesorbitan fatty acid ester. The gels furthermore contain commercially available preservatives, such as benzyl alcohol, phenethyl alcohol, phenoxyethanol and the like.

The following is a list of examples of body care products of this invention and their ingredients:

| Body care product | Ingredients |
| --- | --- |
| moisturising cream | vegetable oil, emulsifier, thickener, perfume, water, antioxidant, uv absorbers |
| shampoo | surfactant, emulsifier, preservatives, perfume, antioxidant, uv absorbers |
| toothpaste | cleaning agent, thickener, sweetener, flavor, colorant, antioxidant, water, uv absorbers |
| lip-care stick | vegetable oil, wax, $TiO_2$, antioxidant, uv absorbers |

The present body care products, household products, textiles and fabrics have high stability towards color changes and chemical degradation of the ingredients present in these products. For example, present compositions that comprise a dye are found to have excellent color stability.

Accordingly, the present invention further pertains to a stabilized composition comprising
(a) a body care product, household product, textile or fabric,
(b) an effective stabilizing amount of at least one compound selected from the group consisting of
   (i) hindered nitroxyl compounds of formula (I),
   (ii) hindered hydroxylamine compounds of formula (II) and
   (iii) hindered hydroxylamine salt compounds of formula (III) and
(d) a dye.

Dyes according to the present invention are for example:
inorganic pigments, for example iron oxide (Iron Oxide Red, Iron Oxide Yellow, Iron Oxide Black, etc.), Ultramarines, Chromium Oxide Green or Carbon Black;
natural or synthetic organic pigments;
disperse dyes which may be solubilized in solvents like direct hair dyes of the HC type, for example HC Red No. 3, HC Blue No. 2 and all other hair dyes listed in International Cosmetic Ingredient Dictionary and Handbook, 7$^{th}$ edition 1997) or the dispersion dyes listed in Color Index International or Society of Dyers and Colourists;
color varnishes (insoluble salts of soluble dyes, like many Ca-, Ba- or Al-salts of anionic dyes);
soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wavelength of ca. 4000 to 700 nm). The absorption is often caused by the following chromophores: Azo- (mono-, di, tris-, or poly-) stilbene-, carotenoide-, diarylmethan-, triarylmethan-, xanthen-, acridin-, quinoline, methin- (also polymethin-), thiazol-, indamin-, indophenol-, azin-, oxazin-, thiazin-, anthraquinone-, indigoid-, phtalocyanine- and further synthetic, natural and/or inorganic chromophores.

The present stabilizer systems are also used in household cleaning and treatment agents, for example in laundry products and fabric softeners, liquid cleansing and scouring agents, glass detergents, neutral cleaners (all-purpose cleaners), acid household cleaners (bath), bathroom cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

The present invention also concerns home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

The stabilizers of the present invention may be employed in fabric treatment that takes place after use of the fabric, referred to as fabric care. Such treatments include laundering, which uses detergents and/or fabric conditioner, and the application of non-detergent based fabric care products, such as spray-on products. When employed in this fashion, the present stabilizers are intended for deposition onto the fabric and used to protect the fabric, colorants and fragrances associated with said these fabrics from environmental damage.

Typical examples of household cleaning and treating agents are:

| Household cleaners/household treating agents | Ingredients |
| --- | --- |
| detergent concentrate | surfactant mixture, ethanol, antioxidant, water, uv absorbers, antioxidant |
| shoe polish | wax, wax emulsifier, antioxidant, water, preservative, uv absorbers, antioxidant |
| wax-containing floor | emulsifier, wax, sodium chloride, antioxidant, water, |
| cleaning agent | preservative, uv absorbers, antioxidant |

The present stabilizers are for example incorporated by dissolution in an oil phase or alcoholic or water phase, where required at elevated temperature.

The present invention also pertains to a method of stabilizing a body care product, household product, textile or fabric, which comprises incorporating therein or applying thereto at least one compound of the formulae (I), (II) and (III), for example at least one compound of the formulae A to EE and A* to EE*.

In the case of stabilized fabrics, for example dyed fabrics, the present stabilizers are applied thereto via deposition from for instance detergents, fabric conditioners or non-detergent based fabric care products.

The present fabrics are natural or synthetic, and may be woven or nonwoven.

The present invention also pertains to a method of stabilizing a body care product, household product, textile or fabric, each of which contain a dye, which comprises incorporating therein or applying thereto at least one compound of the formulae (I), (II) and (III), for example at least one compound of the formulae A to EE and A* to EE*. The stabilizers of formulae (I), (II) and (III) are very effective towards the stabilization of dyes in the present compositions.

The textiles of this invention are for example textile fiber materials, for example nitrogen-containing or hydroxy-group-containing fiber materials, for instance textile fiber materials selected from cellulose, silk, wool, synthetic polyamides, leather and polyurethanes. Included are cotton, linen and hemp, pulp and regenerated cellulose. Included also are cellulosic blends, for example mixtures of cotton and polyamide or cotton/polyester blends.

The additives of the present invention are for example applied to textiles in a dyeing or printing process, or in a finishing process. For instance, the additives may be applied as part of a dye formulation. The additives may be applied to textiles for example h an ink-jet printing process. The additives are for example applied as part of an aqueous dye solution or printing paste. They may be applied in an exhaust method or dyeing by the padder dyeing method, in which the textiles are impregnated with aqueous dye solutions, which may contain salts, and the dyes and additives are fixed, after an alkali treatment or in the presence of alkali, if appropriate with the action of heat or by storage at room temperature for several hours. After fixing, the dyeings or prints are rinsed thoroughly with cold and hot water, if appropriate with the addition of an agent which has a dispersing action and promotes diffusion of the non-fixed portions.

The dye or ink formulations for application to textiles may comprise further customary additives, for example surfactants, antifoams, antimicrobials and the like, for example as disclosed in U.S. Pat. Nos. 6,281,339, 6,353,094 and 6,323,327, the disclosures of which are hereby incorporated by reference.

The following Examples illustrate the invention. Percentages are in weight percent unless indicated otherwise.

The following stabilizers are employed in the Examples:

(A)
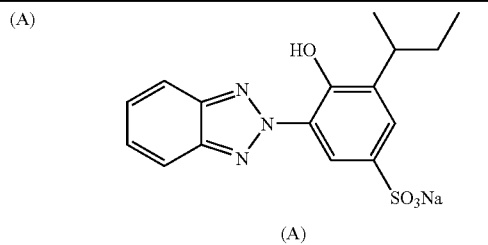

(B)
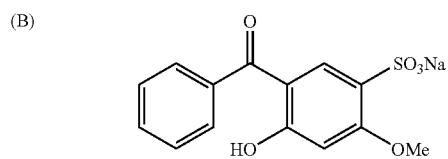

(C)
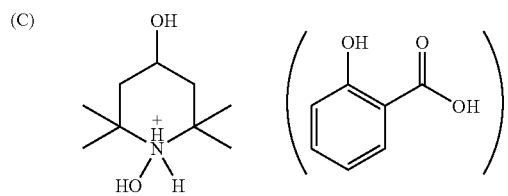

(D)
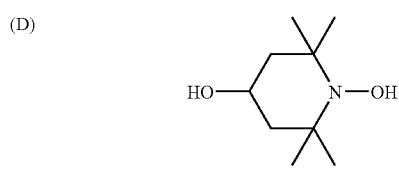

(E)
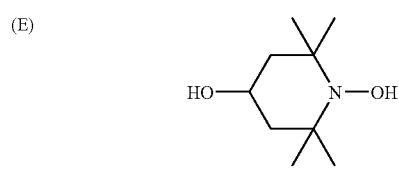

-continued

Aqueous based test formulations are prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant | 0.001% |
| stabilizer | 0.05% |
| citric acid (10% aqueous solution) | to pH 6 |
| deionized water | to 100% |

About 20 ml of each of the aqueous test formulations are placed in a borosilicate glass bottle.

The glass bottles are exposed in an Atlas Ci-65 Xenon arc WetherOmeter, AATCC Test Method 16, option E.

The bottles are also exposed to accelerated fluorescent lighting, Philips, 40 Watt, Daylight Deluxe (D65), full exposure to light.

Color measurements are performed on a Hunter Ultrascan XE spectrophotometer. Delta L, a and b values are the difference between the initial values and the values at each interval. Delta($\Delta$) E is calculated as follows:

$$[(\text{Delta } L)^2 + (\text{Delta } a)^2 + (\text{Delta } b)^2]^{1/2} = \text{Delta } E$$

Example 1

Aqueous Model Formulation with PURICOLOR BLUE ABL9

Aqueous formulations are prepared where the colorant is PURICOLOR BLUE ABL9 (FD&C Blue No. 1). Exposure is in a WeatherOmeter. Delta E is measured at 20-hour intervals. Results are below:

| | delta E | | | | |
|---|---|---|---|---|---|
| stabilizer | 20 hrs. | 40 hrs. | 60 hrs. | 80 hrs. | 100 hrs. |
| none (control) | 47 | — | — | — | — |
| (A) | 46 | — | — | — | — |
| (B) | 47 | — | — | — | — |
| (C) | 4 | 5 | 27 | 49 | — |
| (D) | 1 | 6 | 37 | 47 | — |
| (E) | 1 | 4 | 7 | 11 | 17 |

It is seen that the stabilizers of the present invention, (C), (D) and (E), provide far greater color stability than state of the art stabilizers (A) and (B).

Example 2

Aqueous Model Formulation with PURICOLOR RED ARE33 (D&C Red No. 33)

Aqueous formulations are prepared where the colorant is PURICOLOR RED ARE33. Exposure is in a WeatherOmeter. Delta E is measured at 20 hour intervals. Results are below:

|  | delta E | | | |
| --- | --- | --- | --- | --- |
| stabilizer | 20 hrs. | 40 hrs. | 60 hrs. | 80 hrs. |
| none (control) | 55 | — | — | — |
| (A) | 55 | — | — | — |
| (B) | 55 | — | — | — |
| (C) | 16 | 42 | 56 | — |
| (D) | 13 | 48 | 58 | — |
| (E) | 9 | 14 | 22 | 58 |

It is seen that the stabilizers of the present invention, (C), (D) and (E), provide far greater color stability than state of the art stabilizers (A) and (B).

Example 3

Aqueous Model Formulation with FD&C Red No. 40

Aqueous formulations are prepared where the colorant is FD&C Red No. 40. Exposure is in a WeatherOmeter. Delta E is measured at 20 hour intervals. Results are below:

|  | delta E | | | |
| --- | --- | --- | --- | --- |
| stabilizer | 20 hrs. | 40 hrs. | 60 hrs. | 80 hrs. |
| none (control) | 33 | — | — | — |
| (A) | 33 | — | — | — |
| (B) | 33 | — | — | — |
| (C) | 5 | 12 | 33 | — |
| (D) | 6 | 13 | 33 | — |
| (E) | 4 | 7 | 9 | 10 |

It is seen that the stabilizers of the present invention, (C), (D) and (E), provide far greater color stability than state of the art stabilizers (A) and (B).

Example 4

Aqueous Model Formulation with PURICOLOR BLUE ABL9

Aqueous formulations are prepared where the colorant is PURICOLOR BLUE ABL9. Exposure is to fluorescent light. Delta E is measured at weekly intervals. Results are below:

|  | delta E | | | | | | |
| --- | --- | --- | --- | --- | --- | --- | --- |
| stabilizer | 1 week | 2 weeks | 4 weeks | 5 weeks | 6 weeks | 8 weeks | 14 weeks |
| none (control) | 46 | — | — | — | — | — | — |
| (A) | 46 | — | — | — | — | — | — |
| (B) | 28 | 47 | — | — | — | — | — |
| (C) | 2.4 | 3.4 | 4 | 5 | 8 | 39 | — |
| (D) | 1 | 1 | 2 | 3.4 | 47 | — | — |
| (E) | 0.7 | 1 | 2 | 3 | 5 | 9 | 17 |

It is seen that the stabilizers of the present invention, (C), (D) and (E), provide far greater color stability than state of the art stabilizers (A) and (B).

Example 5

Aqueous Model Formulation with D&C Red No. 33

Aqueous formulations are prepared where the colorant is PURICOLOR RED ARE33 (D&C Red No. 33). Exposure is to fluorescent light. Delta E is measured at weekly intervals. Results are below:

|  | delta E | | | | | |
| --- | --- | --- | --- | --- | --- | --- |
| stabilizer | 1 week | 2 weeks | 4 weeks | 5 weeks | 7 weeks | 8 weeks |
| none (control) | 29 | 55 | — | — | — | — |
| (A) | 18 | 56 | — | — | — | — |
| (B) | 20 | 55 | — | — | — | — |
| (C) | 15 | 23 | 45 | 55 | 8 | 39 |
| (D) | 7 | 12 | 19 | 55 | 47 | — |
| (E) | 5 | 9 | 15 | 19 | 22 | 24 |

It is seen that the stabilizers of the present invention, (C), (D) and (E), provide far greater color stability than state of the art stabilizers (A) and (B).

Example 6

Aqueous Model Formulation with FD&C Red No. 40

Aqueous formulations are prepared where the colorant is FD&C Red No. 40. Exposure is to fluorescent light. Delta E is measured at weekly intervals. Results are below:

| stabilizer | 1 week | 2 weeks | 4 weeks | 5 weeks | 7 weeks | 8 weeks |
| --- | --- | --- | --- | --- | --- | --- |
| none (control) | 33 | — | — | — | — | — |
| (A) | 33 | — | — | — | — | — |
| (B) | 33 | — | — | — | — | — |
| (C) | 3 | 5 | 8 | 11 | 23 | 33 |
| (D) | 3 | 5 | 9 | 11 | 18 | 33 |
| (E) | 2 | 3 | 5 | 7 | 10 | 12 |

It is seen that the stabilizers of the present invention, (C), (D) and (E), provide far greater color stability than state of the art stabilizers (A) and (B).

Example 7

Preparation of a Moisturiser Cream

| Phase | Ingredients | (w/w) % |
| --- | --- | --- |
| A | passionflower oil | 8 |
|  | glyceryl dioleate | 4 |
|  | dicapryl ether | 4 |
|  | isopropylisostearate | 4 |
|  | stabilizer (C), (D) or (E) | 0.05 |
| B | water, demin. | ad. 100 |
|  | EDTA | 0.1 |
| C | carbomer | 0.15 |
| D | sodium hydroxide | 10% 0.20 |
| E | perfume; preservative | q.s. |

The components of phase A are thoroughly mixed in a homogenizer for 10 min at 75-80° C. The water phase B, likewise heated to 75-80° C. beforehand, is slowly added and the mixture is homogenized for 1 min. The mixture is cooled, with stirring, to 40° C. and then phases C and E are added and the mixture is homogenized for 1 min. Subsequently, phase D is added and the mixture is homogenized for ½ min and cooled, with stirring, to room temperature. Excellent results are achieved.

Example 8

Preparation of a Toilet Water (w/w) %

| Ingredients | (w/w) % |
| --- | --- |
| ethanol, 96% | 60 |
| d-limonene | 5 |
| cedrene | 1.5 |
| citronellol | 0.5 |
| savin | 0.5 |
| stabilizer (C), (D) or (E) | 0.08 |
| UV absorber | 0.1 |
| S,S-EDDS | 0.005 |
| colorant (D&C Yellow No. 5) | 0.02 |
| water | ad. 100 |

The components are thoroughly mixed in the cited sequence at 50° C., a clear homogeneous solution being obtained. The UV absorber is one of the present disclosure, for example 3-(2H-benzotriazol-2-yl)-4-hydroxy-5-(1-methylpropyl)-benzenesulfonic acid monosodium salt. Excellent results are achieved.

Example 9

Preparation of a Hair Styling Spray

| Ingredients | (w/w) % |
| --- | --- |
| alcohol, anhydrous | 96.21 |
| octylacrylamide/acrylate/butylaminoethylmethacrylate copolymer | 2.52 |
| hydroxypropyl cellulose | 0.51 |
| aminomethylpropanol (95%) | 0.46 |
| stabilizer (C), (D) or (E) | 0.05 |
| UV absorber | 0.05 |
| perfume oil | 0.20 |

The hydroxypropyl cellulose is first predissolved in half of the alcohol (Vortex mixer) and is charged with the aminomethylpropanol. The other components—with the exception of the acrylate resin—are dissolved in alcohol and this solution is added, with stirring, to the hydroxypropyl cellulose. Subsequently, the acrylate resin is added and stirred until completely dissolved. Benzophenone-4 is 5-benzoyl-4-hydroxy-2-methoxybenzenesulfonic acid, sodium salt. Excellent results are achieved.

Example 10

Preparation of a Shampoo for Greasy Hair

| Ingredients | (w/w) % |
| --- | --- |
| sodium myreth sulfate | 50.00 |
| TEA abietoyl collagen hydrolysate | 3.50 |
| laureth-3 | 3.00 |
| colorant (D&C Red No. 33) | 0.20 |
| stabilizer (C), (D) or (E) | 0.05 |
| UV absorber | 0.15 |
| phosphonomethylchitosan, sodium salt | 0.01 |
| perfume oil | 0.10 |
| water | ad. 100 |

The components are mixed, with stirring, at room temperature until they are completely dissolved. The pH is 6.5. The UV absorber is one of the present disclosure, for example 2-(2-hydroxy-3-dodecyl-5-methylphenyl)-2H-benzotriazole. Excellent results are achieved.

Example 11

Preparation of a Leather Dressing and Cleaning Agent

| Ingredients | (w/w) % |
| --- | --- |
| synthetic soap (Zetesap 813) | 7.85 |
| glycerol | 6.00 |
| anionic surfactant (Lumorol 4192; Mulsifan RT 13) | 22.00 |
| Vaseline | 11.00 |
| paraffin 52/54 | 20.00 |
| talcum | 2.00 |
| orange terpene | 4.00 |
| stabilizer (C), (D) or (E) | 0.02 |
| water | 27.13 |

The stabilizer is predissolved in the terpene. The components are then stirred in the cited sequence at about 65° C. until homogeneous. The mixture is then cooled to room temperature. Excellent results are achieved.

Example 12

Preparation of a Glass Detergent

| Ingredients | (w/w) % |
| --- | --- |
| anionic/amphoteric surfactants (Lumorol RK) | 0.7 |
| butyl glycol | 5.0 |
| Isopropanol | 20.0 |
| d-limonene | 4.00 |
| stabilizer (C), (D) or (E) | 0.02 |
| water, demin. | ad. 100 |

The stabilizer is predissolved in the terpene. The components are then dissolved in the cited sequence until a clear homogeneous mixture is obtained. Excellent results are achieved.

Example 13

Protection of Dyes in Fabrics

Stabilizers (C), (D) and (E) are each deposited (from water) on a dyed cotton fabric at 0.05, 0.1, 0.2, 0.5 and 1.0 percent by weight, based on the weight of the cotton. The dyed fabrics contain the following dyes at 0.05, 0.1, 0.2 and 0.5 percent by weight based on cotton. This results in 60 separate formulations for each dye listed:

| Scarlet HE-3G | Crimson HE-XL | Yellow HE-6G | Red HE-XL |
|---|---|---|---|
| Blue HE-XL | Turquoise H-A | Navy HE-XL | Remazol |
| Red RB | Brilliant Red RBS | Orange FR | Navy CG |
| Turquoise G | Black B | | |

The cotton fabrics are subjected to light exposure in an Atlas Ci-65 Xenon arc WetherOmeter and to accelerated fluorescent lighting. The present stabilizers provide outstanding color protection to the dyed fabrics. This experiment simulates dye protection achievable through deposition of the present stabilizers via treatment with for example stabilizer-containing laundry detergent or fabric conditioner.

Similar dye protection is also afforded to textiles such as wool, silk, leather, cellulosics and polyamides.

What is claimed is:

1. A stabilized composition comprising
   (a) a body care product, household cleaning product, wherein the body care product is selected from the group consisting of:
   skin-care product,
   which skin-care products are selected from the group consisting of body oils, body lotions, body gels, treatment creams, skin protection ointments, shaving preparation and skin powders, bath and shower product, preparations containing fragrances and odoriferous substances,
   hair-care products which hair-care products are selected from the group consisting of shampoos for humans and animals, hair conditioners, 2 in 1 conditioners, leave in and rinse off conditioners, products for styling and treating hair, perming agents, hair sprays and lacquers, hair gels, hair fixatives, relaxants, hair dyeing systems, permanent, demi-permanent, semi-permanent and temporary hair dyeing systems, and hair bleaching agents, dentifrices, deodorizing and antiperspirant preparations,
   cosmetic formulations containing active ingredients, which active ingredients are selected from the group consisting of hormone preparations, vitamin preparations, vegetable extract preparations and antibacterial preparations,
   decorative preparations which decorative preparations are selected from the group consisting of lipsticks, nail varnishes, eye shadows, mascaras, dry and moist make-up, rouge, powders, depilatory agents and suntan lotions, and
   the household cleaning product is selected from the group consisting of liquid cleansing and scouring agents, glass detergents, bathroom cleaners, washing, rinsing and dishwashing agents, kitchen and oven cleaners, clear rinsing agents, dishwasher detergents, shoe polishes, polishing waxes, floor detergents and polishes, metal, glass and ceramic cleaners, furniture and multipurpose polishes and leather and vinyl dressing agent and solid and liquid air fresheners,
   (b) an effective stabilizing amount of 5 to about 10000 ppm, based on the total composition,
   at least one compound selected from the group consisting of
   (iii) hindered hydroxylamine salt compounds of formula

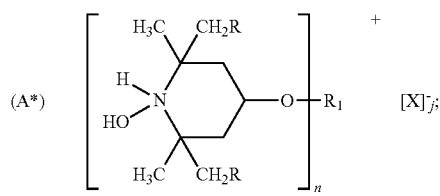

where
in formula A*,
n is 1 or 2,
when n is 1,
$R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —$(COO^-)_n M^{n+}$ where n is 1-3 and M is a metal ion from the 1st, 2nd or 3rd group of the periodic table or is Zn, Cu, Ni or Co, or M is a group $N'''^+(R_2)_4$ where $R_2$ is alkyl of 1 to 8 carbon atoms or benzyl,
when n is 2,
$R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups,
R is hydrogen or methyl;
X is an inorganic or organic anion, and
where the total charge of cations h is equal to the total charge of anions j
and
d) a dye.

2. A composition according to claim 1 where X is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate.

3. A composition according to claim 1 where the compounds of component (b) are
R is hydrogen,
in formula A*
n is 1 or 2,
when n is 1,
$R_1$ is hydrogen, alkyl of 1 to 6 carbon atoms, alkenyl of 2 to 6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or R₁ is alkyl of 1 to 4 carbon atoms substituted by a carboxy group or by —COOZ where Z is hydrogen or alkyl of 1 to 4 carbon atoms,
when n is 2,
R₁ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups.

4. A composition according to 1 where the compounds of component (b) are
R is hydrogen,
in formula A*,
h is 1,
R₁ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
R₁ is alkyl of 1 to 4 carbon atoms substituted by —COOZ where Z is hydrogen or alkyl of 1 to 4 carbon atoms.

5. A composition according to claim 1 where the compounds of component (b) are selected from the group consisting of
1-hydroxyl-2,2,6,6-tetramethyl-4-methoxy-piperidinium acetate; 1-hydroxy-2,2,6,6-tetramethyl-4-propoxy-piperidinium acetate; 1-hydroxy-2,2,6,6-tetramethyl-4-(2-hydroxy-4-oxapentoxy)piperidinium acetate; 1-hydroxy-2,2,6,6-tetramethyl-4-hydroxpiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; tetra(1-hydroxy-2,2,6,6-tetramethyl-4-hydroxypiperidinium) ethylenediaminetetraacetate; penta(1-hydroxy-2,2,6,6-tetramethyl-4-hydroxypiperidinium) diethylenetriaminepentaacetate; tri(1-hydroxy-2,2,6,6-tetramethyl-4-hydroxypiperidinium) nitrilotriacetate; penta(1-hydroxy-2,2,6,6-tetramethyl-4-hydroxypiperidinium) diethylenetriaminepentamethylenephosphonate.

6. A composition according to claim 1 where the compounds of component (b) are selected from the group consisting of 1-hydroxy-2,2,6,6-tetramethyl-4-hydroxypiperidinium chloride; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; tetra(1-hydroxy-2,2,6,6-tetramethyl-4-hydroxypiperidinium) ethylenediaminetetraacetate; penta(1-hydroxy-2,2,6,6-tetramethyl-4-hydroxypiperidinium) diethylenetriaminepentaacetate.

7. A composition according to claim 1 in which the compounds of component (b) are selected from the group consisting of 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; 1-hydroxy-2,2,6,6-tetramethyl-4-hydroxypiperidinium DTPA; bis(1-hydroxy-2,2,6,6-tetramethyl-4-hydroxypiperidinium) DTPA; tris(1-hydroxy-2,2,6,6-tetramethyl-4-hydroxypiperidinium) DTPA; tetrakis(1-hydroxy-2,2,6,6-tetramethyl-4-hydroxypiperidinium) DTPA; pentakis(1-hydroxy-2,2,6,6-tetramethyl-4-hydroxypiperidinium) DTPA; 1-hydroxy-2,2,6,6-tetramethyl-4-hydroxypiperidinium EDTA; bis(1-hydroxy-2,2,6,6-tetramethyl-4-hydroxpiperidinium) EDTA; tris(1-hydroxy-2,2,6,6-tetramethyl-4-hydroxypiperidinium) EDTA; tetrakis(1-hydroxy-2,2,6,6-tetramethyl-4-hydroxypiperidinium) EDTA; and (1-hydroxy-2,2,6,6-tetramethyl-4-hydroxypiperidinium) EDTA.

8. A composition according to claim 1 further comprising (c) at least one compound selected from the group consisting of the ultraviolet light absorbers, antioxidants, tocopherol, tocopherol acetate, hindered amine light stabilizers, complex formers, optical brighteners, surfactants, and polyorganosiloxanes.

9. A composition according to claim 8 where the ultraviolet light absorbers are selected from group consisting of the 2H-benzotriazoles, the s-triazines, the benzophenones, the α-cyanoacrylates, the oxanilides, the benzoxazinones, the benzoates and the α-alkyl cinnamates.

10. A composition according to claim 1 where the compounds of component (b) are present in a concentration of about 10 to about 5000 ppm.

11. A composition according to claim 1 wherein the preparations containing fragrances and olfactory substances are selected from scents, perfumes, toilet waters and shaving lotions.

* * * * *